(12) United States Patent
Poelstra et al.

(10) Patent No.: US 10,987,142 B2
(45) Date of Patent: Apr. 27, 2021

(54) PELVIC WEDGE

(71) Applicant: K2M, Inc., Leesburg, VA (US)

(72) Inventors: Kornelis Poelstra, Los Gatos, CA (US); Greg Anderson, Villanova, PA (US); Josh Rubin, Reston, VA (US); Mary Hayles, Brockport, NY (US); Michael Schular, Gainesville, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/055,497

(22) Filed: Aug. 6, 2018

(65) Prior Publication Data

US 2019/0038329 A1 Feb. 7, 2019

Related U.S. Application Data

(60) Provisional application No. 62/541,152, filed on Aug. 4, 2017.

(51) Int. Cl.
*A61B 17/80* (2006.01)
*A61F 2/28* (2006.01)
(Continued)

(52) U.S. Cl.
CPC ...... *A61B 17/8095* (2013.01); *A61B 17/8066* (2013.01); *A61B 17/86* (2013.01); *A61F 2/28* (2013.01); *A61B 2017/561* (2013.01); *A61F 2/2846* (2013.01); *A61F 2/30734* (2013.01); *A61F 2/30749* (2013.01); *A61F 2/30771* (2013.01); *A61F 2/4684* (2013.01); *A61F 2002/3092* (2013.01); *A61F 2002/3093* (2013.01); *A61F 2002/30156* (2013.01);
(Continued)

(58) Field of Classification Search
CPC ................................ A61B 17/80; A61B 17/86
See application file for complete search history.

(56) References Cited

U.S. PATENT DOCUMENTS 5,397,364 A 3/1995 Kozak et al.
7,232,464 B2 6/2007 Mathieu et al.
(Continued)

OTHER PUBLICATIONS

Styrker Spine: AVS Anchor-C Cervical Cage System; 2014; 2 pages.
(Continued)

*Primary Examiner* — Matthew W Schall
(74) *Attorney, Agent, or Firm* — Lerner, David, Littenberg, Krumholz & Mentlik, LLP

(57) ABSTRACT

A surgical implant assembly includes a surgical implant, a bone plate, and fixation devices. The surgical implant includes a top surface, a bottom surface disposed in opposed relation relative to the top surface, first and second surfaces interconnecting the top and bottom surfaces, and a front surface. First ends of the first and second side surfaces define a back surface extending across a first end of the surgical implant, and the front surface extends across a second end of the surgical implant and interconnects second ends of the first and second side surfaces. At least one cavity is defined in the surgical implant. The bone plate includes an elongate body extending between first and second end portions. The elongate body is positionable adjacent the front surface of the surgical implant. The fixation devices are configured to secure the surgical implant or the bone plate to osseous tissue.

24 Claims, 11 Drawing Sheets

(51) Int. Cl.
*A61B 17/86* (2006.01)
*A61F 2/30* (2006.01)
*A61B 17/56* (2006.01)
*A61F 2/46* (2006.01)

(52) U.S. Cl.
CPC ............... *A61F 2002/30158* (2013.01); *A61F 2002/30179* (2013.01); *A61F 2002/30273* (2013.01); *A61F 2002/30736* (2013.01); *A61F 2002/30784* (2013.01); *A61F 2002/30904* (2013.01); *A61F 2002/4681* (2013.01)

(56) References Cited

U.S. PATENT DOCUMENTS

| | | |
|---|---|---|
| 7,846,207 B2 | 12/2010 | Lechmann et al. |
| 8,801,791 B2 | 8/2014 | Soo et al. |
| 9,480,577 B2 | 11/2016 | Despiau et al. |
| 9,987,051 B2 | 6/2018 | Nunley et al. |
| 2016/0000486 A1 | 1/2016 | Leduc et al. |
| 2016/0213485 A1 | 7/2016 | Schaufler et al. |
| 2016/0213487 A1 | 7/2016 | Wilson et al. |
| 2016/0213488 A1 | 7/2016 | Moore et al. |
| 2017/0360488 A1* | 12/2017 | Kowalczyk ........ A61B 17/8095 |

OTHER PUBLICATIONS

Nuvasive: Speed of Innovation: Brigade: Standalone ALIF: Surgical Technique; 2015, 28 pages.

DePuy Synthes, companies of Johnson & Johnson—Zero-P VA Surgical Technique, 2016, 52 pages.

* cited by examiner

PELVIC WEDGE

CROSS-REFERENCE TO RELATED APPLICATIONS

This application claims the benefit of, and priority to, U.S. Provisional Patent Application Ser. No. 62/541,152, filed on Aug. 4, 2017, the entire content of which is hereby incorporated herein by reference.

TECHNICAL FIELD

The present disclosure relates generally to orthopedic surgical devices, and more particularly, to surgical implants, surgical implant systems, and methods of securing the same to osseous tissue.

BACKGROUND

Patients may undergo surgical procedures, including implanting hardware, to correct various spinal deformities. Despite the implanted hardware, the patient may not regain full balance of their spine and pelvis. Balance parameters of the spine and pelvis have an impact on diagnosis and strategy of spinal pathology treatment. Some of the balance parameters include pelvic parameters, such as pelvic incidence, pelvic tilt, and sacral slope; spinal parameters, such as lumbar lordosis and thoracic kyphosis; and other parameters, such as C7 positioning and sacro-spinal angle.

One approach to correct these balance issues is to completely correct the spinal parameters or revise the original implantation surgery. However, this can be complex, expensive, and time consuming in terms of the surgery and the recovery. Pelvic osteotomy is an alternative surgical procedure that can aid in restoring the balance parameters of the spine and pelvis. There are several types of known pelvic osteotomies, including the Salter procedure, the double or triple innominate, the spherical acetabular procedure, the periacetabular procedure, and the Chiari's procedure. Thus, surgical implants and surgical implant systems for use in osteotomy to treat imbalance of the pelvis and the spine are desirable.

SUMMARY

In accordance with an aspect of the present disclosure, a surgical implant assembly includes a surgical implant, a bone plate, and fixation devices. The surgical implant includes a top surface, a bottom surface disposed in opposed relation relative to the top surface, first and second surfaces interconnecting the top and bottom surfaces, and a front surface. First ends of the first and second side surfaces define a back surface extending across a first end of the surgical implant, and the front surface extends across a second end of the surgical implant and interconnects second ends of the first and second side surfaces. At least one cavity is defined in the surgical implant. The bone plate includes an elongate body extending between first and second end portions. The elongate body of the bone plate is positionable adjacent the front surface of the surgical implant. The fixation devices are configured to secure the surgical implant or the bone plate to osseous tissue and are insertable through opening in the surgical implant or openings in the bone plate.

The surgical implant may have a generally triangular shape and include an angle defined between the first and second side surfaces at the first end of the surgical implant. The angle may be from about 10° to about 45°.

The top and/or bottom surface of the surgical implant may be non-planar. The top surface may have a convex shape and/or the bottom surface may include an inflection point defining a first portion having a convex shape and a second portion having a concave shape.

The surgical implant may have a length extending along a longitudinal axis from the first end of the surgical implant to the second end of the surgical implant. The length may range from about 35 mm to about 95 mm.

The surgical implant may have a variable width. The surgical implant may include a first width extending across the first end of the surgical implant and a second width extending across a first section of the surgical implant disposed adjacent to the first end. The second width may be greater than the first width. The surgical implant may include a third width extending across a second section of the surgical implant disposed adjacent to the second end and a fourth width extending across the second end of the surgical implant. The second width may be greater than the fourth width. The first width may be greater than the fourth width.

The surgical implant assembly may include a bone growth material disposed within the at least one cavity of the surgical implant. The at least one cavity of the surgical implant may include a first cavity disposed in a first section of the surgical implant and a second cavity disposed in a second section of the surgical implant in axial spaced relation relative to the first cavity. The first cavity may have a substantially triangular shape and the second cavity may have a substantially trapezoidal shape. The first and second cavities may extend through and be open at the first and second side surfaces.

The surgical implant may further include at least one channel defined in the surgical implant. The at least one channel may be in fluid communication with the at least one cavity. The at least one channel may extend through and be open at the front surface, pass into the at least one cavity, and extend through and be open at the first or second side surface. The at least one channel may include first and second channels extending through the surgical implant in an x-shaped configuration.

At least a portion of one of the top surface, the bottom surface, the first side surface, the second side surface, or the front side surface of the surgical implant may have a textured finish.

The elongate body of the bone plate may be flat and the first and second end portions of the bone plate may be curved. The first and second end portions may curve in opposite directions.

The surgical implant assembly may further include an attachment screw for securing the bone plate to the surgical implant.

In accordance with another aspect of the present disclosure, a method of implanting a surgical implant into osseous tissue includes forming an opening in an osseous tissue, inserting a surgical implant into the opening formed in the osseous tissue, and inserting at least one fixation device through the surgical implant to anchor the surgical implant within the osseous tissue. The surgical implant includes a top surface, a bottom surface disposed in opposed relation relative to the top surface, first and second surfaces interconnecting the top and bottom surfaces, and a front surface. First ends of the first and second side surfaces define a back surface extending across a first end of the surgical implant, and the front surface extends across a second end of the surgical implant and interconnects second ends of the first and second side surfaces. At least one cavity is defined in the surgical implant.

The method may include attaching a bone plate to the front surface of the surgical implant. The method may further include inserting fixation devices through first and second end portions of the bone plate to anchor the bone plate to the osseous tissue.

The method may include filling the at least one cavity of the surgical implant with a bone growth material.

Other aspects, features, and advantages will be apparent from the description, the drawings, and the claims.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein.

DETAILED DESCRIPTION

Figure 1A:
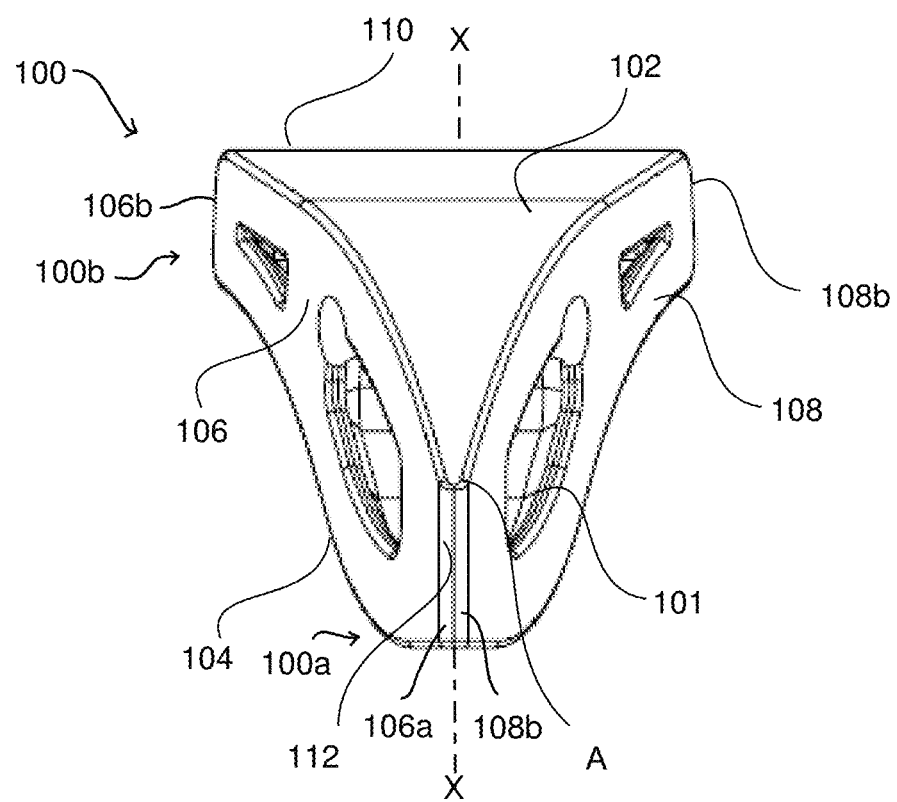
FIG. 1A is a perspective view of a surgical implant in accordance with an embodiment of the present disclosure.

Exemplary embodiments of the present disclosure are discussed herein below in terms of surgical implants and surgical implant systems or assemblies for use in osseous tissue. While the principles of the present disclosure are described below with respect to the insertion of the surgical implants and the surgical implant systems into pelvic bone during an osteotomy, it should be understood that the surgical implants and the surgical implant systems of the present disclosure are suitable for insertion into any osseous tissue and/or use in a variety of surgical procedures. Accordingly, a person of ordinary skill in the art will readily appreciate that the size and/or shape of the surgical implants and the surgical implant systems, or components thereof, can be modified for proper alignment and fit within a desired osseous tissue.

Embodiments of the present disclosure will now be described in detail with reference to the drawings in which like reference numerals designate identical or corresponding elements in each of the several views. Throughout this description, the term "proximal" refers to a portion of a system, a device, or a component thereof, that is closer to a user, and the term "distal" refers to a portion of the system, the device, or the component thereof, that is farther from the user. Additionally, in the drawings and in the description that follows, terms such as "front," "back," "upper," "lower," "top," "bottom," "side," and similar directional terms are used for convenience of description and are not intended to limit the disclosure.

Figure 1B:
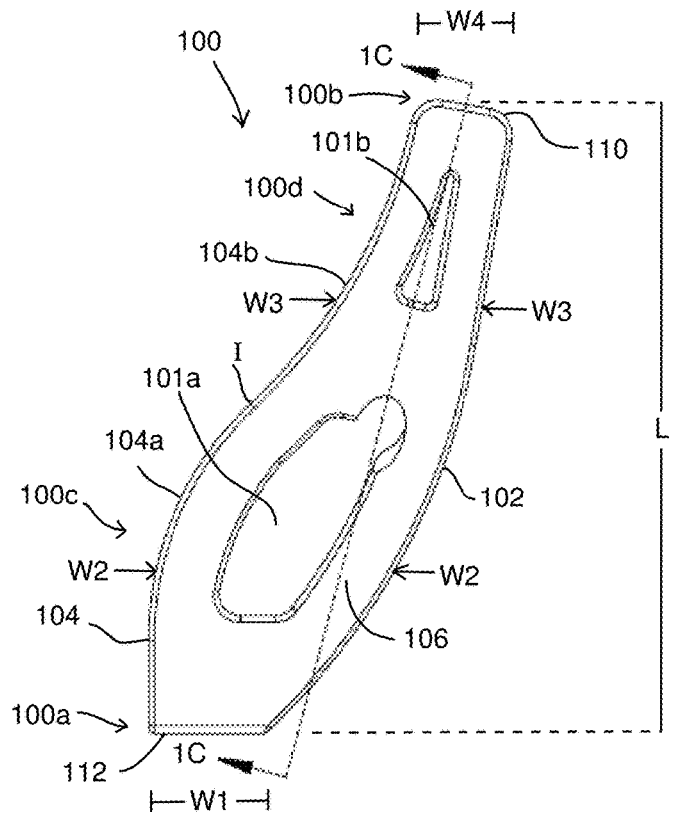
FIG. 1B is a side view of the surgical implant of FIG. 1A.
Figure 1C:
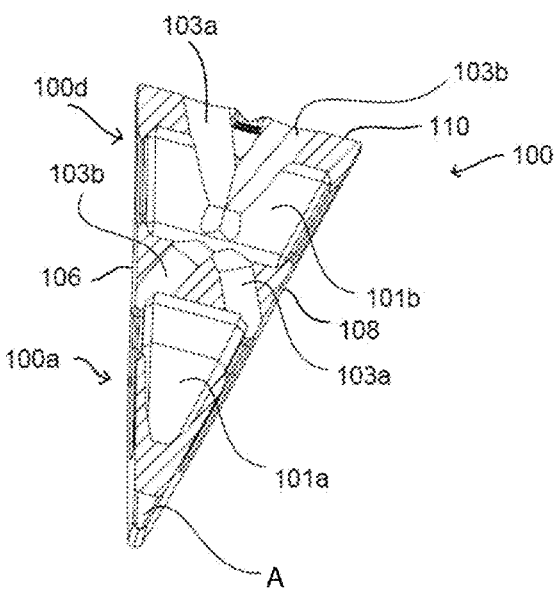
FIG. 1C is a cross-sectional view of the surgical implant of FIG. 1A, taken along section line 1C-1C of FIG. 1B.

Referring now to FIGS. 1A-1C, a surgical implant 100 in accordance with an embodiment of the present disclosure is shown. The surgical implant 100 includes a top surface 102, a bottom surface 104, a first side surface 106, a second side surface 108, a front surface 110, and a back surface 112. The top surface 102 and the bottom surface 104 are disposed in opposed, spaced relation relative to each other, and are interconnected around their perimeter by the first side surface 106, the second side surface 108, the front surface 110, and the back surface 112. Together, the top surface 102, the bottom surface 104, the first side surface 106, the second side surface 108, the front surface 110, and the back surface 112 define at least one cavity 101 within the surgical implant 100.

The surgical implant 100 is formed from biocompatible material(s) including, but not limited to, metals and metal alloys, such as stainless steel, cobalt chrome, titanium, and titanium alloys, as well as polymers, such as polyether ether ketone ("PEEK"), or combinations of the aforementioned materials. The surgical implant 100 may be made using an additive manufacturing process, for example, by printing or foaming material(s) having sufficient strength, resiliency, and biocompatibility as needed or desired for a surgical procedure. For a detailed description of additive manufacturing processes suitable for forming the surgical implant 100, reference can be made to U.S. Patent Appl. Pub. No.

2016/0213485 to Schaufler et al., U.S. Patent Appl. Pub. No. 2016/0213487 to Wilson et al., U.S. Patent Appl. Pub. No. 2016/0213488 to Moore et al., and U.S. Pat. No. 9,987,051 to Nunley et al., the entire content of each of which is hereby incorporated by reference herein.

The first and second side surfaces 106, 108 of the surgical implant 100 are disposed in opposed relation relative to each other and interconnect the top and bottom surfaces 102, 104. First ends 106a, 108a of the first and second side surfaces 106, 108 abut each other and define the back surface 112, which is disposed at a first end 100a of the surgical implant 100. The front surface 110 is disposed at a second end 100b of the surgical implant 100 and extends between second ends 106b, 108b of the first and second side surfaces 106, 108.

The surgical implant 100 has a substantially triangular or wedge shape and defines an angle "A" at the first end 100a of the surgical implant 100 between the first and second side surfaces 106, 108. In embodiments, the angle "A" ranges from about 10° to about 45° and, in some embodiments, the angle "A" ranges from about 15° to about 40° and, in certain embodiments, the angle "A" is about 20°. It should be understood the surgical implant 100 may have any suitable angle "A" for a given surgical procedure, for example, to change the pelvic incidence without the need to remove any hardware present along a vertebra and/or to correct or improve any balance issues in a sagittal or coronal plane.

Figure 7:
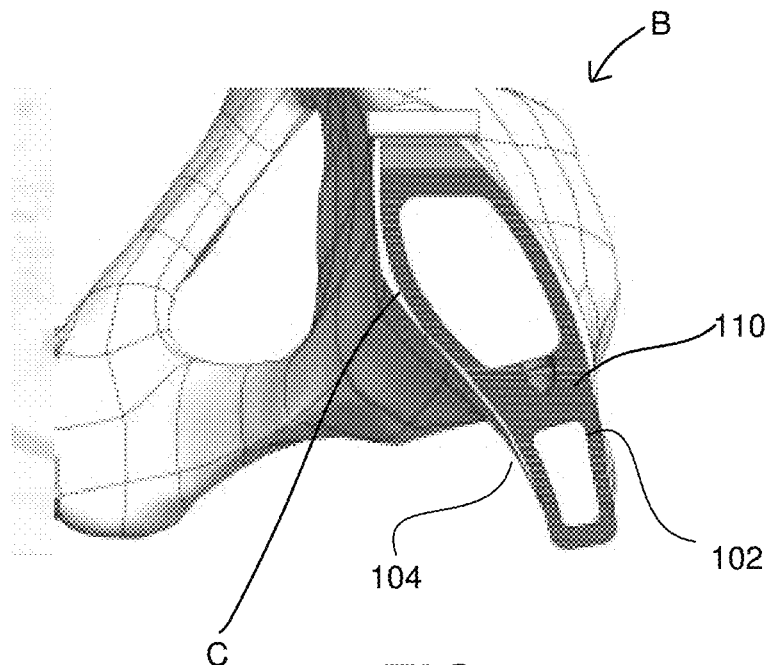
FIG. 7 is a close-up view of the pelvic bone of FIG. 6, illustrating the surgical implant of FIG. 1A positioned in the opening in the pelvic bone.

The top and bottom surfaces 102, 104 of the surgical implant 100 are contoured to mimic or conform to osseous tissue into or against which the surgical implant 100 is to be placed, such as pelvic bone "B" as shown, for example, in FIG. 7. As seen in FIG. 1B, the top surface 102 of the surgical implant 100 has a convex shape and the bottom surface 104 includes an inflection point "I" defining a first portion 104a having a convex shape and a second portion 104b having a concave shape. It should be understood that the radius of curvature of the top and/or bottom surfaces 102, 104 can vary depending upon, for example, the size and shape of the osseous tissue into or against which the surgical implant 100 is positioned.

With reference to FIGS. 1A and 1B, the surgical implant 100 defines a longitudinal axis "X" extending from the first end 100a of the surgical implant 100 about the center of the back surface 112 to the second end 100b of the surgical implant 100 about the center of the front surface 110. The length "L" of the surgical implant 100 along the longitudinal axis "X" may range from about 35 mm to about 95 mm. In embodiments, the length "L" ranges from about 40 mm to about 90 mm and, in some embodiments, the length "L" ranges from about 45 mm to about 85 mm and, in certain embodiments, the length "L" ranges from about 50 mm to about 80 mm. It should be understood that a surgical implant 100 may have any suitable length "L."

The surgical implant 100 defines a variable width along the length "L" of the surgical implant 100. The surgical implant 100 includes a first width "W1" extending across the back surface 112 at the first end 100a of the surgical implant 100, a second width "W2" extending across a first section 100c of the surgical implant 100 disposed adjacent to the first end 100a and that includes a first cavity 101a defined therein, a third width "W3" extending across a second section 100d of the surgical implant 100 disposed adjacent to the second end 100b and that includes a second cavity 101b defined therein, and a fourth width "W4" extending across the front surface 110 of the surgical implant 100 at the second end 100b of the surgical implant 100.

The first width "W1" at the first end 100a of the surgical implant 100 may be wider than the fourth width "W4" at the second end 100b of the surgical implant 100, and/or the surgical implant 100 may be widest at the second width "W2." For example, as shown in FIG. 1B, the width of the surgical implant 100 may increase from the first width "W1" to the second width "W2," taper to the third width "W3," and taper further to the fourth width "W4." It should be understood that a surgical implant 100 may have any suitable width or variable width profile.

The first width "W1" of the surgical implant 100 may range from about 10 mm to about 40 mm. In embodiments, the first width "W1" ranges from about 20 mm to about 30 mm and, in some embodiments, the first width "W1" is about 25 mm. The second width "W2" of the surgical implant 100 may range from about 15 mm to about 45 mm. In embodiments, the second width "W2" ranges from about 20 mm to about 40 mm and, in some embodiments, the second width "W2" is about 35 mm. The third width "W3" of the surgical implant 100 may range from about 10 mm to about 40 mm. In embodiments, the third width "W3" ranges from about 12 mm to about 35 mm and, in some embodiments, the third width "W3" is about 25 mm. The fourth width "W4" of the surgical implant 100 may range from about 2 mm to about 22 mm. In embodiments, the fourth width "W4" ranges from about 7 mm to about 17 mm and, in some embodiments, the fourth width "W4" is about 12 mm.

The at least one cavity 101 of the surgical implant 100 can reduce the density and/or the stiffness of the surgical implant 100. The at least one cavity 101 may be any shape including, for example, round, oblong, or square, and/or may be defined by concave surfaces. The at least one cavity 101 can extend through one or more surfaces (e.g., the first and second side surfaces 106, 108) of the surgical implant 100. It should be understood that a surgical implant 100 may include at least one cavity 101 of any suitable size and geometry.

The surgical implant 100 can further include at least one channel 103 defined therein. The at least one channel 103 can be in fluid communication with the at least one cavity 101. By varying the size and/or shape of the at least one cavity 101 and the at least one channel 103, one can design a surgical implant 100 with a complex internal geometry thereby increasing the surface area within the surgical implant 100. An increase in surface area may increase the rate at which the surgical implant 100 fuses with surrounding osseous tissue and/or may improve securement of the surgical implant 100 to the osseous tissue.

The at least one cavity 101 and/or the at least one channel 103 can be configured and dimensioned to receive a bone growth material 105 (FIG. 10) therein. As used herein, a "bone growth material" can be any material that facilitates osteogenesis. Suitable bone growth materials can be resorbable or non-resorbable, osteoconductive or osteoinductive, and combinations thereof. Non-limiting examples of suitable bone growth materials include synthetic materials, bone morphogenic proteins, and heterologous, homologous, or autologous bone and derivatives thereof.

As shown in FIGS. 1A-1C, the surgical implant 100 includes a first cavity 101a having a substantially triangular shape disposed in the first section 100c of the surgical implant 100 and a second cavity 101b having a substantially trapezoidal shape disposed in the second section 100d of the surgical implant 100 in axial spaced relation relative to the first cavity 101a. Each of the first and second cavities 101a, 101b extends through and is open at the first and second side surfaces 106, 108 of the surgical implant 100. It should be understood that the number of cavities in the surgical implant 100 may vary (e.g., the surgical implant 100 may include one cavity or more than two cavities of the same or different geometries).

Figures 3A, 3B:
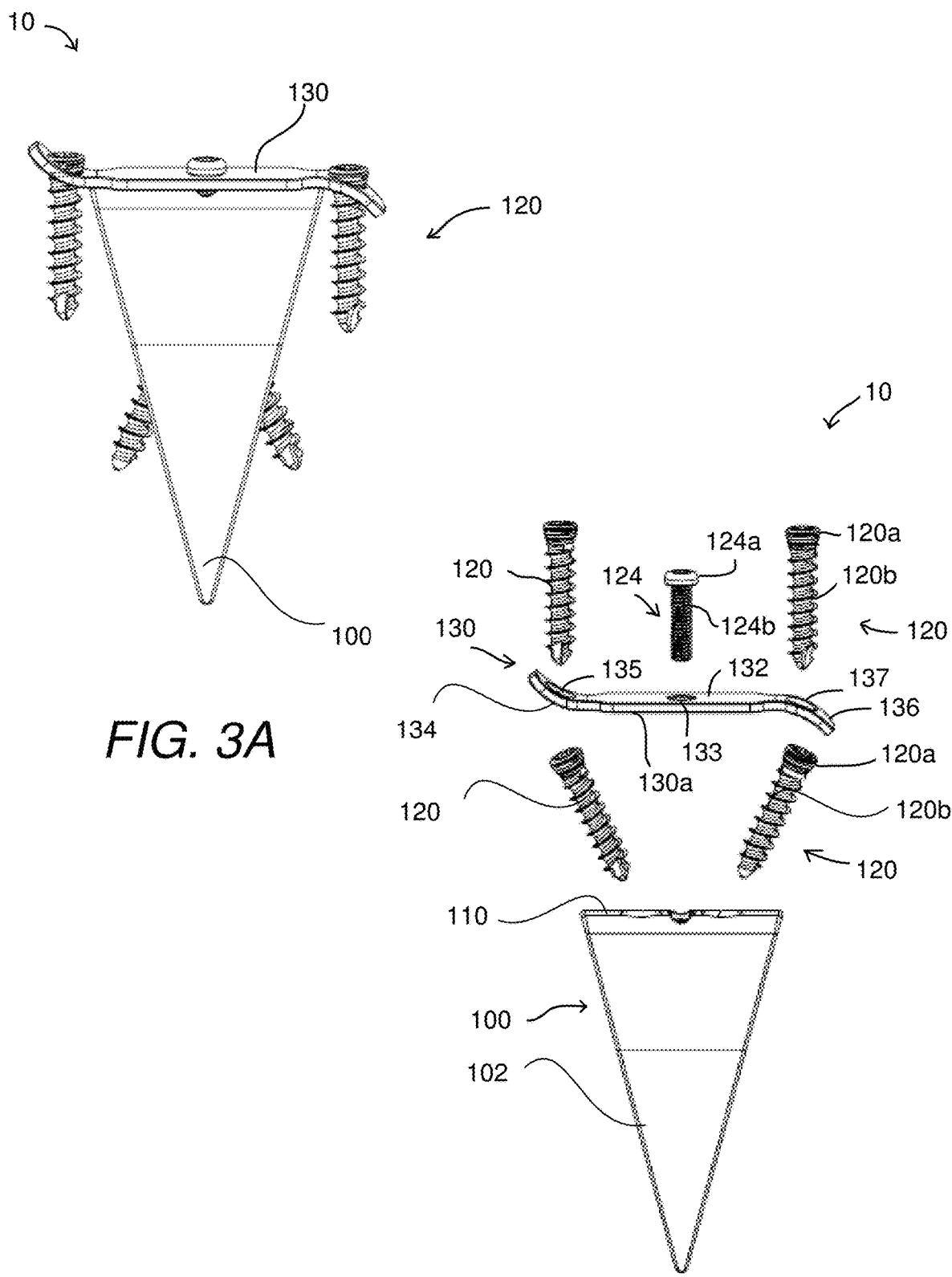
FIG. 3A is a top view of a surgical implant system including the surgical implant of FIG. 1A, a bone plate, and fixation devices in accordance with an embodiment of the present disclosure.
FIG. 3B is an exploded view of the surgical implant system of FIG. 3A.
Figures 3C, 3D:
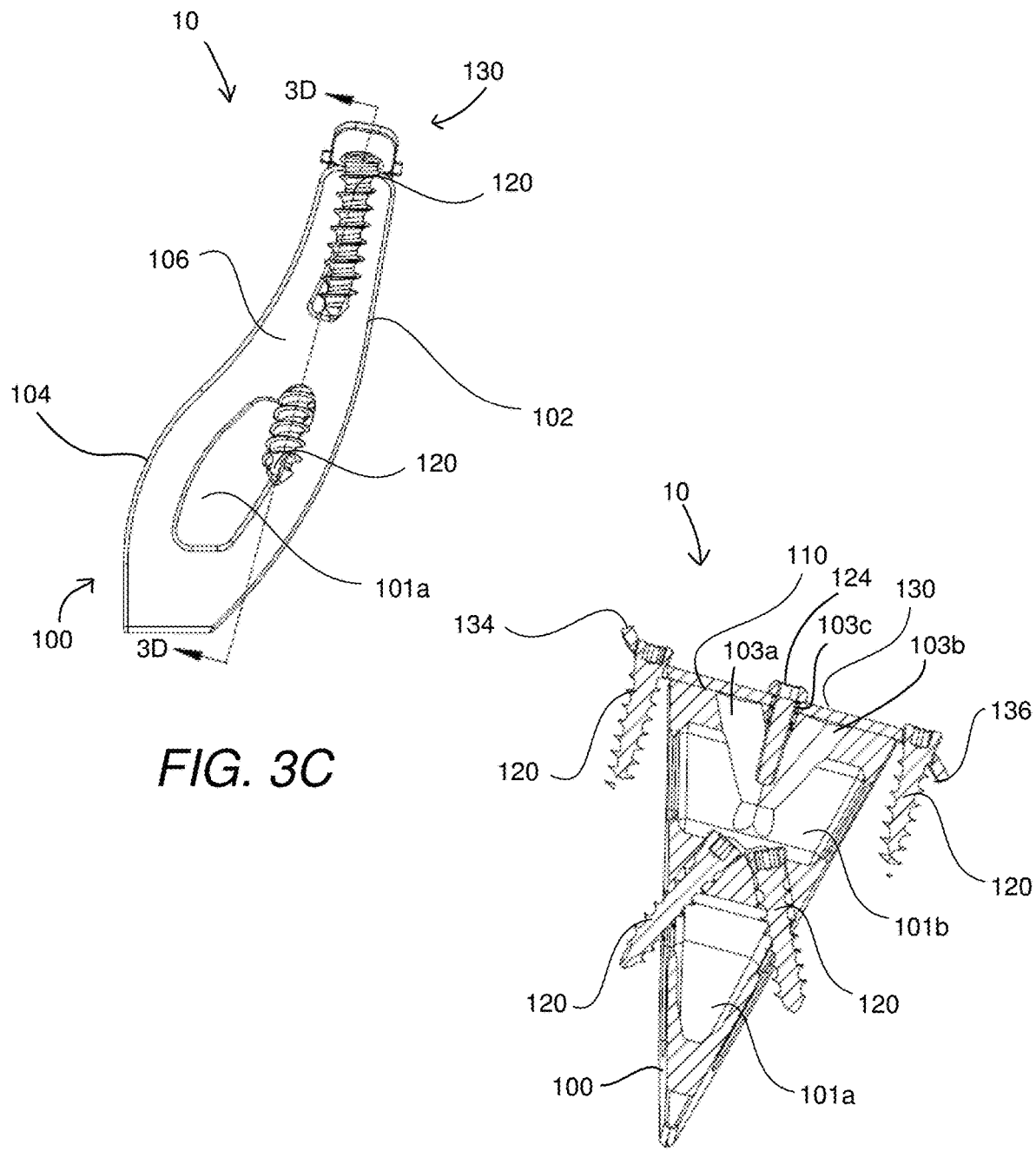
FIG. 3C is a side view of the surgical implant system of FIG. 3A.
FIG. 3D is a cross-sectional view of the surgical implant system of FIG. 3A, taken along line 3D-3D of FIG. 3C.

As seen in FIG. 1C, first and second channels 103a, 103b extend through the surgical implant 100 in an x-shaped configuration interconnecting the first and second cavities 101a, 101b. The first and second channels 103a, 103b extend through and are open at the front surface 110 of the surgical implant 100, pass into and/or through the first and second cavities 101a, 101b and cross each other within the interior of the surgical implant 100, and extend through and are open at the first and second side surfaces 106, 108 of the surgical implant 100. The first and second channels 103a, 103b may intersect each other, or may be separate and distinct from each other. The first and second channels 103a, 103b can be configured and dimensioned to receive at least one fixation device 120 therethrough (see e.g., FIG. 3D).

The surgical implant 100 can include a smooth finish (see e.g., FIGS. 1A-1C) or a textured finish (see e.g., FIGS. 2A and 2B) over a portion or the entirety of at least one of the top surface 102, the bottom surface 104, the first side surface 106, the second side surface 108, the front surface 110, or the back surface 112. The smooth or textured finish may additionally or alternatively be disposed on interior walls defining the first and/or second cavities 101a, 101b of the surgical implant 100.

A textured finish can promote bone growth and fusion with the surgical implant 100. The textured finish may extend across at least about 10% of the respective surface on which it is disposed. In embodiments, the textured finish extends across at least 75% of the respective surface and, in some embodiments, the textured finish extends across at least about 90% of the respective surface.

Figure 2A:
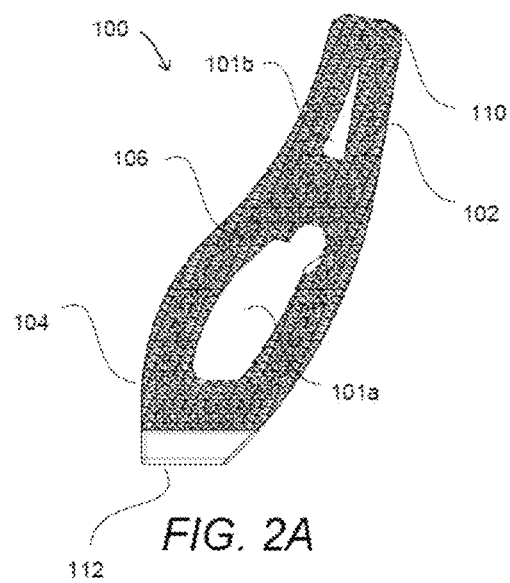
FIG. 2A is a side view of a surgical implant in accordance with another embodiment of the present disclosure, showing a textured surface of the surgical implant including surface roughness.
Figure 2B:
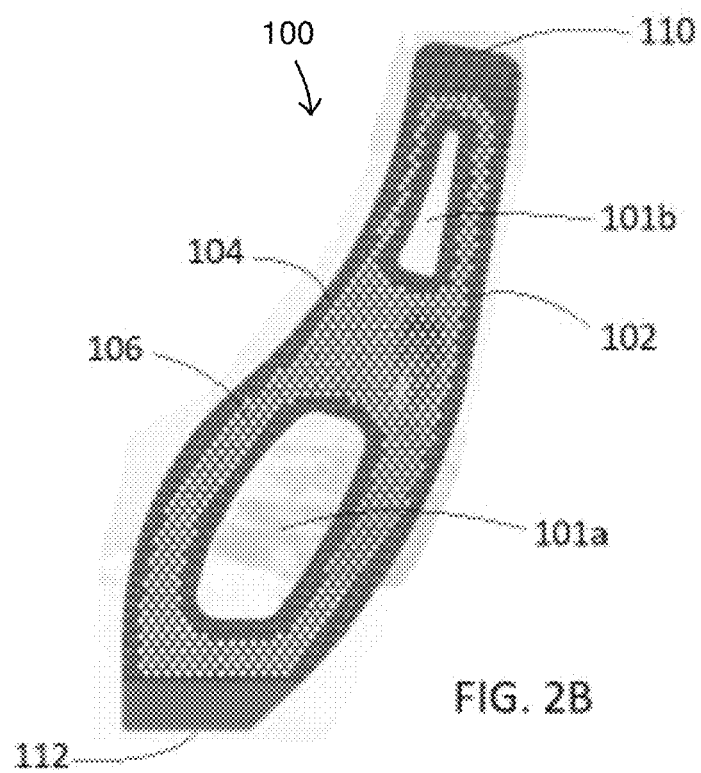
FIG. 2B is a side view of a surgical implant in accordance with yet another embodiment of the present disclosure, showing a textured surface of the surgical implant including pores.

The textured finish can provide the surgical implant 100 with a surface roughness as shown, for example, in FIG. 2A, and/or a porosity as shown, for example, in FIG. 2B, to improve adhesion between the surgical implant 100 and osseous tissue and/or facilitate bony integration with a biomaterial (e.g., bone growth material) to achieve bone fixation at the interface between the surgical implant 100 and the osseous tissue. The pores may extend partially into the surface in which the pores are formed or may extend entirely through the surface and be open to the at least one cavity 101 of the surgical implant 100. The textured finish may be formed by subjecting a smooth surface to a surface roughening treatment such as, etching, sand blasting, etc. The textured finished may be structured and define, for example, a surface including substantially pyramidal protrusions where each pyramidal protrusion includes a plurality of protrusions or ridges disposed thereon to aid in securing the surgical implant 100 to osseous tissue. In particular, each pyramidal protrusion can include opposed first and second faces that face, respectively, distally and proximally, and opposed third and fourth faces that face, respectively, medially and laterally. For a detailed description of a surgical device having exemplary surface characteristics suitable for use with the surgical implant 100, reference can be made to U.S. Pat. No. 8,801,791 to Soo et al., the entire content of which is hereby incorporated by reference herein.

With reference now to FIGS. 3A-3D, the surgical implant 100 can be part of a surgical implant system or assembly 10. The surgical implant system 10 includes the surgical implant 100 and fixation devices or bone screws 120. The fixation devices 120 are used to secure the surgical implant 100 to osseous tissue. Each of the fixation devices 120 includes a head 120a and a threaded shank 120b extending from the head 120a. The fixation devices 120 may be self-tapping or self-starting screws. The fixation devices 120 are positionable through the surgical implant 100 via the first and second channels 103a, 103b such that the heads 120a are disposed within the surgical implant 100 and the threaded shanks 120b extend through respective first and second side surfaces 106, 108 of the surgical implant 100 at an angle with respect to the longitudinal axis "X" of the surgical implant 100.

Figure 4A:
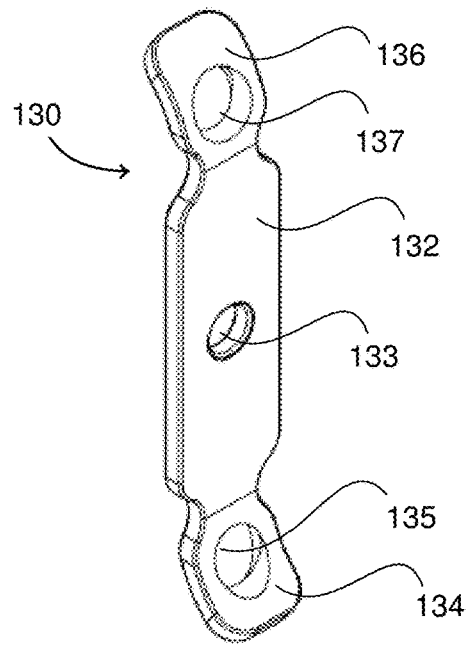
FIG. 4A is a perspective view of the bone plate of the surgical implant system of FIG. 3A.
Figure 4B:
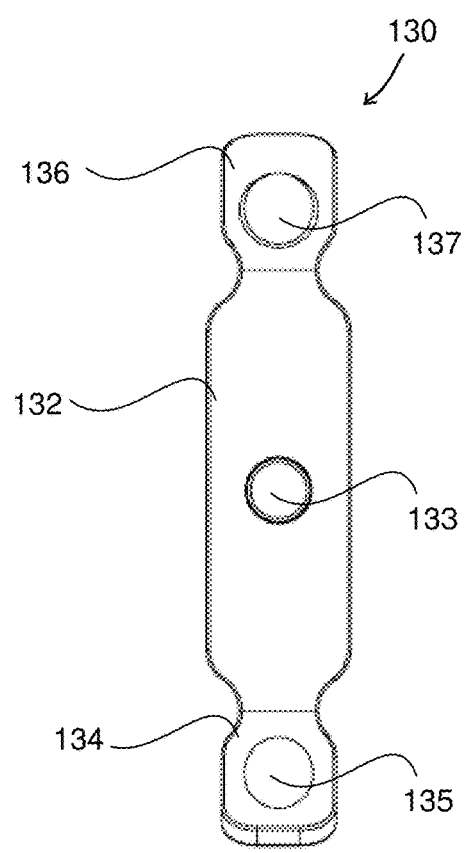
FIG. 4B is a front view of the bone plate of FIG. 4A.
Figure 4C:
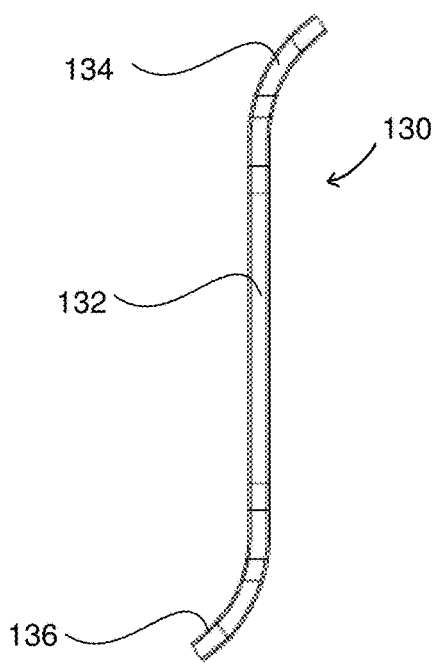
FIG. 4C is a side view of the bone plate of FIG. 4A.

The surgical implant system 10 can further a bone plate 130. As shown in FIGS. 4A-4C, the bone plate 130 includes an elongate body 132 extending between a first end portion 134 and a second end portion 136. The elongate body 132 is flat (i.e., planar), and the first and second end portions 134 are curved. The curve of the first end portion 134 may be the reverse of the curve of the second end portion 136 such that the radius of curvature of the first end portion 134 is opposite the radius of curvature of the second end portion 136. The curvature of each of the first and second end portions 134, 136 can mimic the curvature of osseous tissue against which the bone plate 130 is to be placed such that the first and second end portion 134, 136 conform to the osseous tissue. In embodiments, one of the first or second end portions 134, 136 may be curved and the other flat.

The elongate body 132 of the bone plate 130 can include a central opening 133 defined therethrough, and the first and second end portions 134, 136 can include respective apertures 135, 137 defined therethrough. The central opening 133 and/or the apertures 135, 137 may be configured for use with the fixation devices 120 (see e.g., FIG. 3B) of the surgical implant system 10 for securing the bone plate 130 to the surgical implant 100 or to osseous tissue.

With reference again to FIGS. 3A-3D, the bone plate 130 is positionable against and attachable to the surgical implant 100. The bone plate 130 may be mated with the front surface 110 of the surgical implant 100. An attachment screw 124 may be used to secure the surgical implant 100 and the bone plate 130 together. The attachment screw 124 includes a head 124a and a threaded shank 124b extending from the head 124a. The attachment screw 124 may be a machine screw. The attachment screw 124 is positioned through the central aperture 133 of the bone plate 130 such that the head 124a is secured against the bone plate 130 and the threaded shank 124b is engaged with the surgical implant 100 (e.g., the threaded shank 124 of the attachment screw 124 may engage pre-formed threads defined in a third channel 103c of the surgical implant 100). Alternatively, the bone plate 130 may be integral with the surgical implant 100.

Figure 5A:
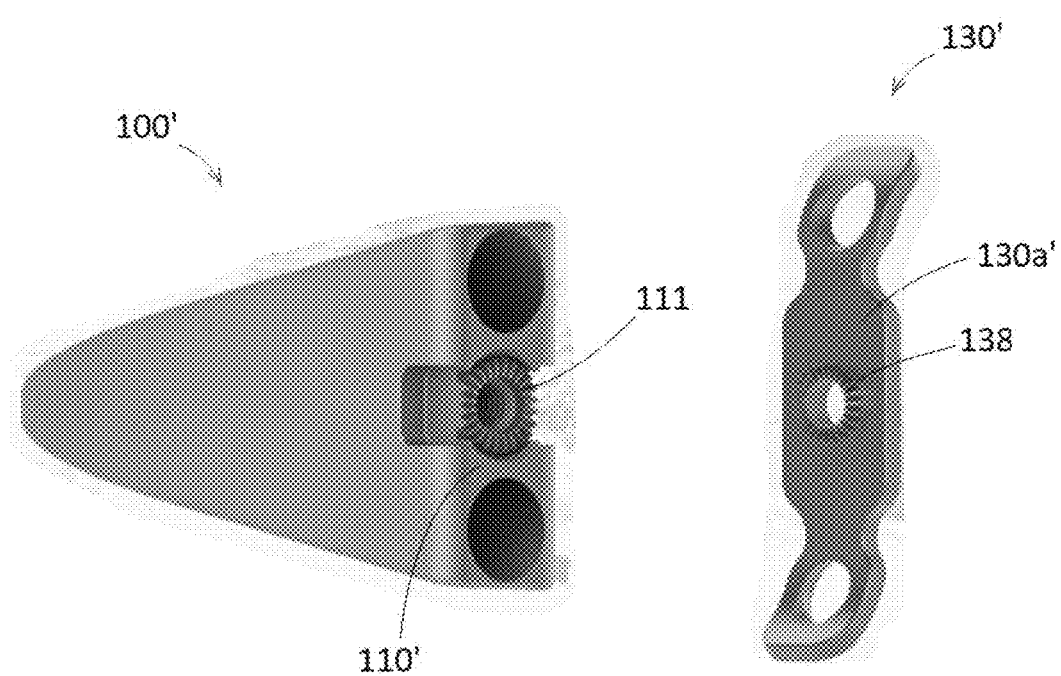
FIG. 5A is a perspective view of a surgical implant and a bone plate in accordance with another embodiment of the present disclosure.

The bone plate 130 may include a textured bottom surface 130a that can mate or interlock with a textured finish disposed on the front surface 110 of the surgical implant 100. As shown in FIG. 5A, a bone plate 130' may include raised teeth or ridges 138 extending from a bottom surface 130a' of the bone plate 130' that are complementary and configured to engage teeth or ridges 111 disposed on the front surface 110' of the surgical implant 100'. The teeth 138 of the bone plate 130' and the teeth 111 of the surgical implant 100' may be disposed in an annular configuration such that a user can adjust the positioning of the bone plate 130 relative to the surgical implant 100 by rotating the bone plate 130 and engaging different ridges or teeth. This allows the bone plate 130' to rotate in fixed increments relative to the surgical implant 100.

Figure 5B:
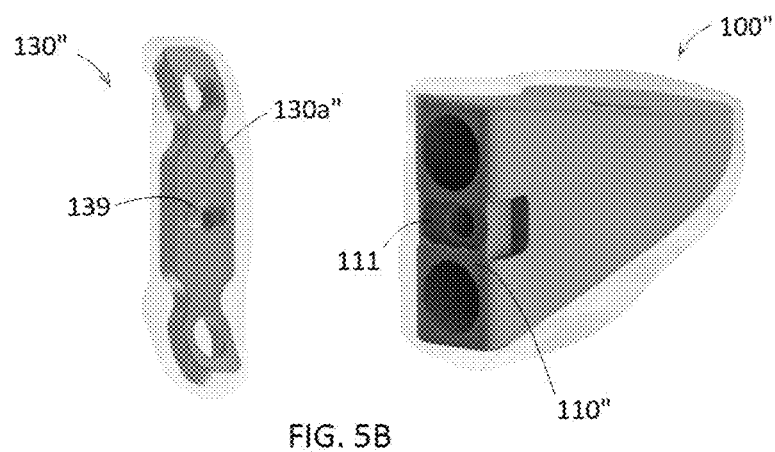
FIG. 5B is a perspective view of a surgical implant and a bone plate in accordance with yet another embodiment of the present disclosure.
Figure 5C:
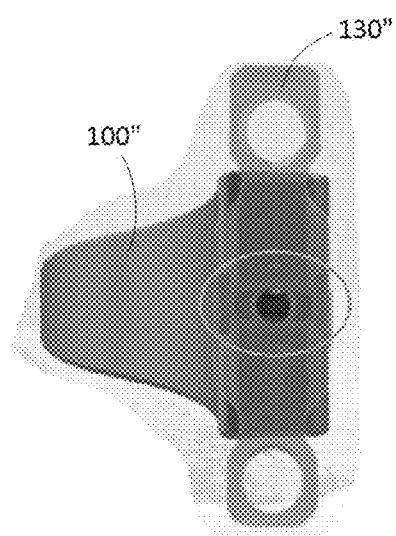
FIGS. 5C-5E are front views of the surgical implant and the bone plate of FIG. 5B, showing the bone plate rotated at different orientations relative to the surgical implant.

In another embodiment shown in FIG. 5B, the bottom surface 130a" of the bone plate 130" may include a key 139 and the front surface 130" of the surgical implant 100" may include a slot 111 that are configured to mate such that the key 139 can be positioned in the slot 131, as shown in FIG.

Figure 5D:
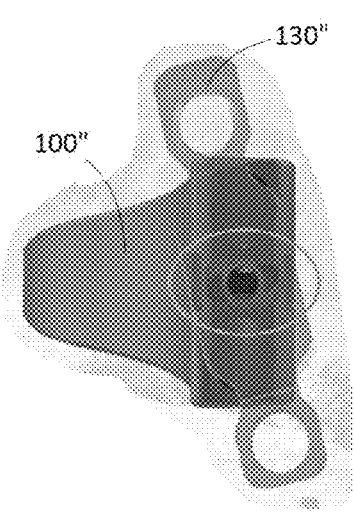
Figure 5E:
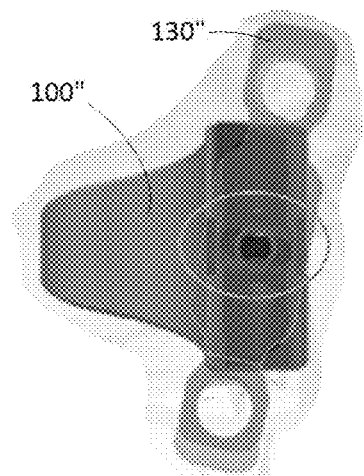

5C, and rotated therein as shown in FIGS. 5D and 5E. The slot 131 may limit the range of rotation of the bone plate 130" to about +/−30°, and in some embodiments, the range of rotation is about +/−15°. Alternatively, the bone plate 130 and the surgical implant 100 can have smooth surfaces that allow for free rotation or limited friction therebetween.

With reference again to FIGS. 3A-3D, two bone screws 120 are used for securing the bone plate 130 to osseous tissue. The bone screws 120 are positionable through the respective apertures 135, 137 of the bone plate 130 such that the heads 120a are secured against the bone plate 130 and the threaded shanks 120b extend therethrough.

The bone plate 130 can have a length that is longer than a length of the front surface 110 of the surgical implant 100. For example, the length of the body 132 of the bone plate 130 may correspond with the length of the front surface 110 of the surgical implant 100 such that the first and second end portions 134, 136 of the bone plate 130 extend laterally beyond the surgical implant 100. In such a configuration, the bone screws 120 are positionable through the bone plate 130 such that the heads 120a are secured against the bone plate 130 and the threaded shanks 120b extend into osseous tissue against which the bone plate 130 is seated (see e.g., FIG. 9). Alternatively, the length of the bone plate 130 can be equal to the length of the front surface 110 of the surgical implant 100.

Figure 6:
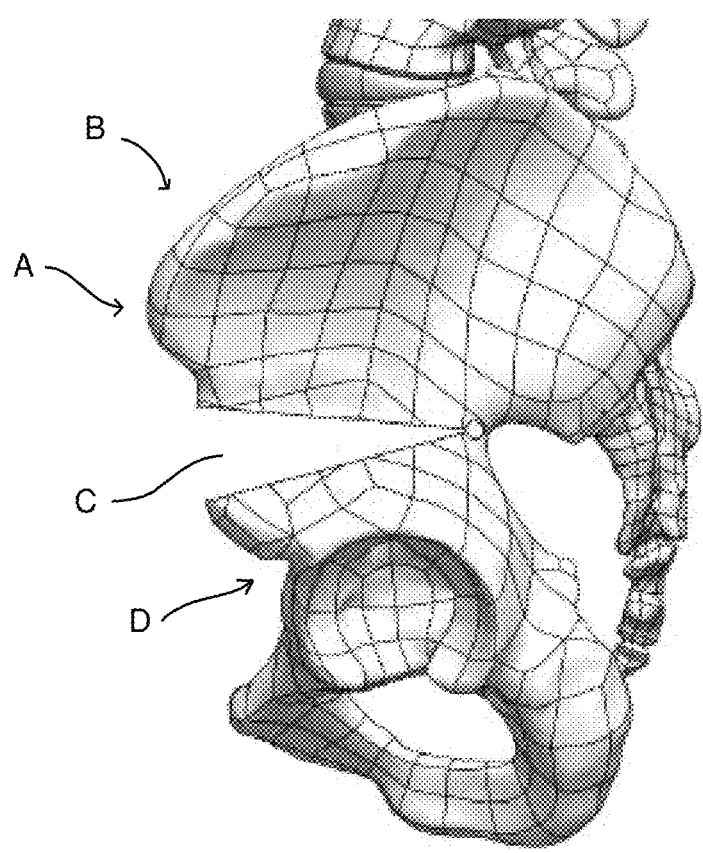
FIG. 6 is a side view of a pelvic bone, illustrating an opening formed therein in accordance with an embodiment of the present disclosure.

A method of implanting or installing the surgical implant 100 in accordance with an embodiment of the present disclosure includes preparing an opening or cut "C" in osseous tissue, such as a pelvic bone "B," as shown in FIG. 6, using devices and/or techniques within the purview of those skilled in the art (e.g., cutting, drilling, milling, grinding, etc.). For example, taking an anterior approach, a standard incision may be made and retractors may be utilized to expose the iliac spine bi-laterally. A cut may then be made between the anterior superior iliac spine "A" and the anterior inferior iliac spine "D", leaving about 10 mm of pelvic bone "B" intact on the posterior end of the incision. An osteotome (e.g., a hinged osteotome) may then be utilized to distract the pelvic bone "B" and form the opening "C" therein.

The surgical implant 100 is then inserted into the opening "C" of the pelvic bone "B," as shown in FIG. 7, to maintain the opening "C." In embodiments, trial implants may be utilized for initial fitting and size confirmation. An appropriately sized surgical implant 100 is chosen which can be securely seated within the opening "C" and forms a tight fit with the distracted pelvic bone "B." The contours of the surgical implant 100 may match the opening "C" formed in the pelvic bone "B" to improve stability and congruity between the surgical implant 100 and the pelvic bone "B." In embodiments, the first cavity 101a of the surgical implant 100 may be packed with bone growth material prior to implantation. The surgical implant 100 may be inserted into the opening "C" utilizing an inserter, as well as a mallet and straight impactor. X-ray or fluoroscopy may be used to verify placement of the surgical implant 100 in the pelvic bone "B."

Figure 8:
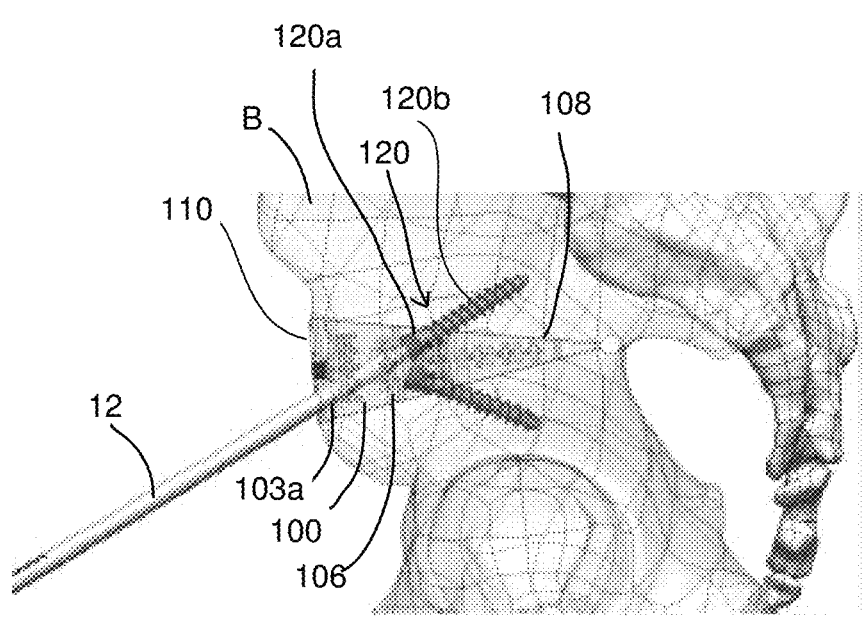
FIG. 8 is a side view of the pelvic bone and a side cross-sectional view of the surgical implant of FIG. 7, illustrating the insertion of fixation devices into the surgical implant.

At least one fixation device 120 may then be inserted into the surgical implant 100 to secure the surgical implant 100 to the pelvic bone "B." As shown in FIG. 8, one of the fixation devices 120 is inserted into the first channel 103a of the surgical implant 100 until the threaded shank 120b of the fixation device 120 passes through the second side wall 108 of the surgical implant 100 and into the pelvic bone "B," and then another of the fixation devices 120 is inserted into the second channel 103b of the surgical implant 100 until the threaded shank 120b of the fixation device 120 passes through the first side wall 106 and into the pelvic bone "B." A driving instrument 12 can be inserted into the head 120a of the fixation device 120 to aid in the insertion of the fixation devices 120 through the surgical implant 100 and into the pelvic bone "B." A user can apply a rotation force to the fixation device 120 using the driving instrument 12 to anchor the fixation device 120 into the pelvic bone "B." Further, the user can apply an opposite rotational force to the fixation device 120 using the driving instrument 12 to adjust the placement of the fixation device 120 within the pelvic bone "B" or to remove the fixation device 120 completely therefrom. TIFIX® locking technology may be utilized to secure the fixation device 120 to the bone plate 130 once the fixation device 120 is properly positioned in the surgical implant 100. After the fixation device 120 is properly positioned in the surgical implant 100, the second cavity 101b of the surgical implant 100 may be packed with bone growth material.

Figure 9:
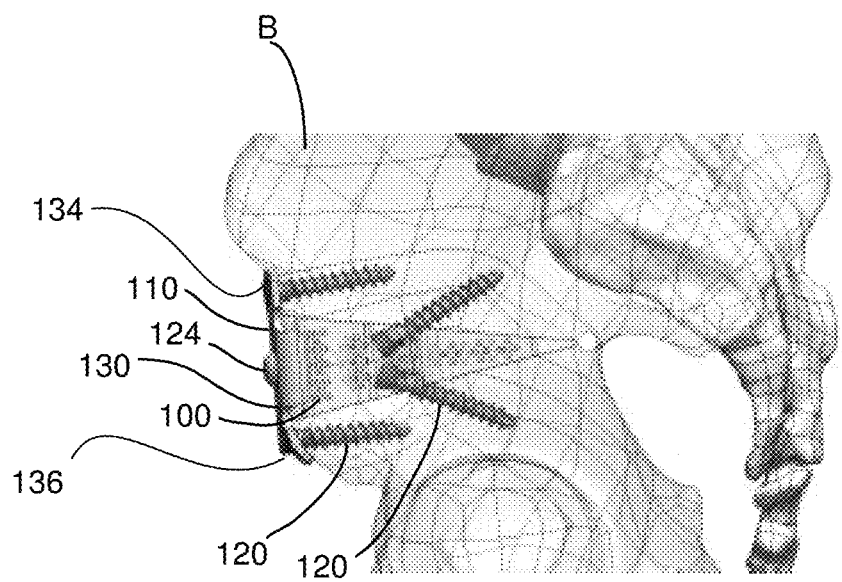
FIG. 9 is a side view of the pelvic bone and a side cross-sectional view of the surgical implant of FIG. 7, illustrating the bone plate and fixation devices of the surgical implant system of FIG. 3A attached to the surgical implant and the pelvic bone, in accordance with an embodiment of the present disclosure.
Figure 10:
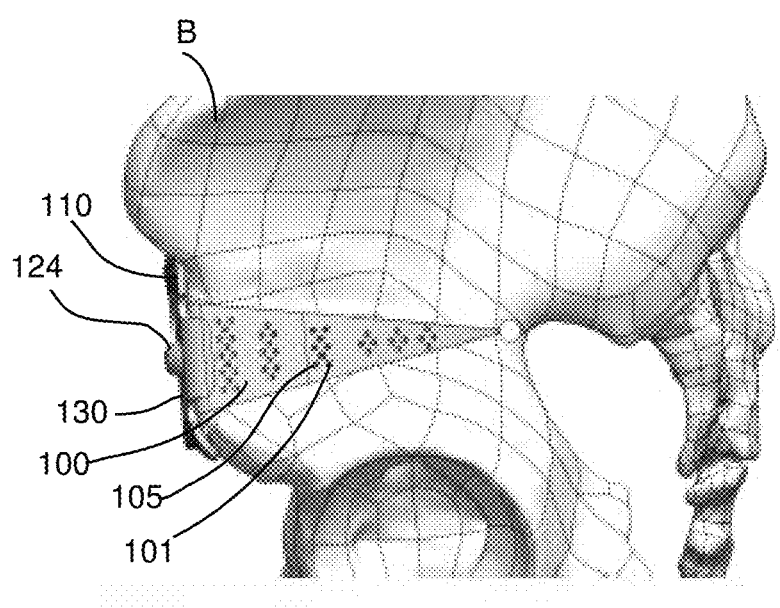
FIG. 10 is a side view of the pelvic bone and a side cross-sectional view of the surgical implant of FIG. 7, illustrating bone growth material disposed within at least one cavity of the surgical implant and the bone plate of FIG. 4A attached to the surgical implant and the pelvic bone, in accordance with another embodiment of the present disclosure.

With the surgical implant 100 installed into the pelvic bone "B," as discussed above, the method can further include attaching a bone plate 130 to the surgical implant 100, as shown in FIGS. 9 and 10. In embodiments, trial plates may be utilized for initial fitting and size confirmation. The bone plate 130 may be placed adjacent the front surface 110 of the surgical implant 100 and the attachment screw 124 may be inserted through the central opening 133 of the bone plate 130 and into the surgical implant 100 to secure the bone plate 130 thereto. The orientation of the bone plate 130 relative to the surgical implant 100 may be adjusted prior to tightening the attachment screw 124 to, for example, ensure that the first and second end portions 134, 136 of the bone plate 130 are contoured to the outer surface of the pelvic bone "B." A plate holder may be utilized to seat the bone plate 130 flush against the pelvic bone "B." Fixation devices 120 may then be inserted through the respective apertures 135, 137 of the first and second end portions 134, 136 of the bone plate 130 and into the pelvic bone "B" to anchor the bone plate 130 against the pelvic bone "B" using, for example, the driving instrument 12 (FIG. 8). A standard wound closure procedure may then be used to complete the procedure.

The surgical implant 100 or the surgical implant system 10 may be provided in a kit. The kit is an assembled package including at least one surgical implant 100 and at least one fixation device 120. The kit may further include at least one bone plate 130. In embodiments, the kit includes a plurality of surgical implants 100 of various sizes (e.g., surgical implants having different lengths and/or widths), a plurality of fixation devices 120 of various lengths (e.g., 45 mm, 60 mm, etc.) and types (e.g., low-profile head screws, rounded-head screws, pins, shims, wedges, blades, etc.), and/or a plurality of bone plates 130 of various configurations to allow a user to pick and choose one or more suitable components for a surgical procedure. The kit may include a first container or compartment including the at least one surgical implant 100 and a second container or compartment including the at least one fixation device 120. The kit may further include a third container or compartment including the at least one bone plate 130.

It is envisioned that the surgical implant 100 may be solid, open-faced, and/or expandable. The surgical implant 100 may be expanded by an active or passive mechanism and/or include a height expansion/reduction mechanism to allow for dynamic changes to the height and/or length of the surgical implant 100. It is contemplated that the changes in the height and/or length can alter the angle "A" of the surgical implant 100 to accommodate or correct patient anatomy. The surgical implant 100 can be built in-situ by a user inside of osseous tissue to tailor the surgical implant 100 to conform to the anatomy of an individual patient.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described. Thus, other embodiments are within the scope of the following claims.

What is claimed is:

1. A surgical implant assembly comprising:
   a surgical implant including:
      a top surface;
      a bottom surface disposed in opposed relation relative to the top surface;
      first and second side surfaces interconnecting the top and bottom surfaces, first ends of the first and second side surfaces defining a back surface extending across a first end of the surgical implant;
      a front surface extending across a second end of the surgical implant and interconnecting second ends of the first and second side surfaces;
      at least one cavity defined in the surgical implant;
      a first channel defined in the surgical implant, the first channel extending from the front surface to the at least one cavity and oriented at an acute angle relative to the front surface; and
      a second channel defined in the surgical implant, the second channel extending from the at least one cavity to one of the first and second side surfaces, the second channel being in alignment with the first channel such that a first axis coincides with central axes of the first and second channels,
      wherein the first channel and the second channel are in fluid communication with the at least one cavity:
   a bone plate including an elongate body extending between first and second end portions, the elongate body positionable adjacent the front surface of the surgical implant; and
   fixation devices configured to secure the surgical implant or the bone plate to osseous tissue, the fixation devices insertable through the first and second channels in the surgical implant or openings in the bone plate.

2. The surgical implant assembly according to claim 1, wherein the surgical implant has a generally triangular shape including an angle defined between the first and second side surfaces at the first end of the surgical implant.

3. The surgical implant assembly according to claim 2, wherein the angle is from about 10° to about 45°.

4. The surgical implant assembly according to claim 1, wherein the top and bottom surfaces of the surgical implant are non-planar.

5. The surgical implant assembly according to claim 4, wherein the top surface has a convex shape.

6. The surgical implant assembly according to claim 4, wherein the bottom surface includes an inflection point defining a first portion having a convex shape and a second portion having a concave shape.

7. The surgical implant assembly according to claim 1, wherein the surgical implant has a length extending along a longitudinal axis from the first end of the surgical implant to the second end of the surgical implant, the length ranging from about 35 mm to about 95 mm.

8. The surgical implant assembly according to claim 1, wherein the surgical implant has a varying width.

9. The surgical implant assembly according to claim 8, wherein the surgical implant includes a first width extending across the first end of the surgical implant and a second width extending across a first section of the surgical implant disposed adjacent to the first end, the second width being greater than the first width.

10. The surgical implant assembly according to claim 9, wherein the surgical implant includes a third width extending across a second section of the surgical implant disposed adjacent to the second end and a fourth width extending across the second end of the surgical implant, the second width being greater than the fourth width.

11. The surgical implant assembly according to claim 10, wherein the first width is greater than the fourth width.

12. The surgical implant assembly according to claim 1, further including a bone growth material disposed within the at least one cavity of the surgical implant.

13. The surgical implant assembly according to claim 1, wherein the at least one cavity of the surgical implant includes a first cavity disposed in a first section of the surgical implant and a second cavity disposed in a second section of the surgical implant in axial spaced relation relative to the first cavity.

14. The surgical implant assembly according to claim 13, wherein the first cavity has a substantially triangular shape and the second cavity has a substantially trapezoidal shape.

15. The surgical implant assembly according to claim 13, wherein the first and second cavities extend through and are open at the first and second side surfaces.

16. The surgical implant assembly according to claim 1, where the at least one channel includes first and second channels extending through the surgical implant in an x-shaped configuration.

17. The surgical implant assembly according to claim 1, wherein at least a portion of one of the top surface, the bottom surface, the first side surface, the second side surface, or the front side surface of the surgical implant has a textured finish.

18. The surgical implant assembly according to claim 1, wherein the elongate body of the bone plate is flat and the first and second end portions are curved.

19. The surgical implant assembly according to claim 18, wherein the first and second end portions curve in opposite directions.

20. The surgical implant assembly according to claim 1, further including an attachment screw for securing the bone plate to the surgical implant.

21. A method f implanting surgical implant into osseous tissue comprising:
   forming an opening in an osseous tissue;
   inserting a surgical implant into the opening formed in the osseous tissue, the surgical implant including:
      a top surface;

a bottom surface disposed in opposed relation relative to the top surface;

first and second side surfaces interconnecting the top and bottom surfaces, first ends of the first and second side surfaces defining a back surface extending across a first. end of the surgical implant;

a front surface extending across a second end of the surgical implant and interconnecting second ends of the first and second side surfaces;

at least one cavity defined in the surgical implant;

a first channel defined in the surgical implant, the first channel extending from the front surface to the at least one cavity and oriented at an acute angle relative to the front surface; and a second channel defined in the surgical implant, the second channel extending from the at least one cavity to one of the first and second side surfaces, the second channel being in alignment with the first channel such that a first axis coincides with central axes of the first and second channels, wherein the first channel and the second channel are in fluid communication with the at least one cavity; and inserting at least one fixation device through the surgical implant to anchor the surgical implant within the osseous tissue.

22. The method according to claim 21, further comprising attaching a bone plate to the front surface of the surgical implant.

23. The method according to claim 22. further comprising inserting fixation devices through first and second end portions of the bone plate to anchor the bone plate to the osseous tissue.

24. The method according to claim 21, further comprising filling the at least one cavity of the surgical implant with a bone growth material.

* * * * *